United States Patent [19]

Blu et al.

[11] 4,154,099
[45] May 15, 1979

[54] PROCESS AND DEVICE FOR MEASURING THE RATIO OF THE SPECIFIC HEATS OF A FLUID AT A CONSTANT PRESSURE AND A CONSTANT VOLUME

[75] Inventors: Gilbert Blu, Paris; Flavien Lazarre; Gilles Le Tetour, both of Pau, all of France

[73] Assignee: Societe Nationale Elf Aquitaine (Production), Paris, France

[21] Appl. No.: 899,660

[22] Filed: Apr. 24, 1978

[30] Foreign Application Priority Data

Apr. 26, 1977 [FR] France .............................. 77 12519

[51] Int. Cl.$^2$ .......................................... G01K 17/00
[52] U.S. Cl. ................................................ 73/190 R
[58] Field of Search ..................................... 73/190 R

[56] References Cited

PUBLICATIONS

Collins, "New Approach to the Measurement of Specific Heat of Gases", Rev. of Sci. Inst., vol. 26, No. 6, Jun. 1955.

Livesey, Univ. of British Columbia, "Apparatus for Measuring the Specific Heat of a Gas", Jun. 26, 1964.

Primary Examiner—Anthony V. Ciarlante
Attorney, Agent, or Firm—Bacon & Thomas

[57] ABSTRACT

The invention is related to a method of measuring the ratio $\gamma$ of the specific heats of a fluid at a given constant pressure $C_P$ and a constant volume $C_V$ corresponding to a given temperature $T_o$ and a given pressure $P_o$. This method comprises the steps of adiabatically compressing a predetermined mass of the fluid to be examined, detecting the maximum pressure value $P_S$, measuring said maximum pressure value, measuring the stabilization pressure $P_T$ and computing the specific heat ratio according to the equation:

$$\gamma = (P_S - P_o)/(P_T - P_o).$$

10 Claims, 7 Drawing Figures

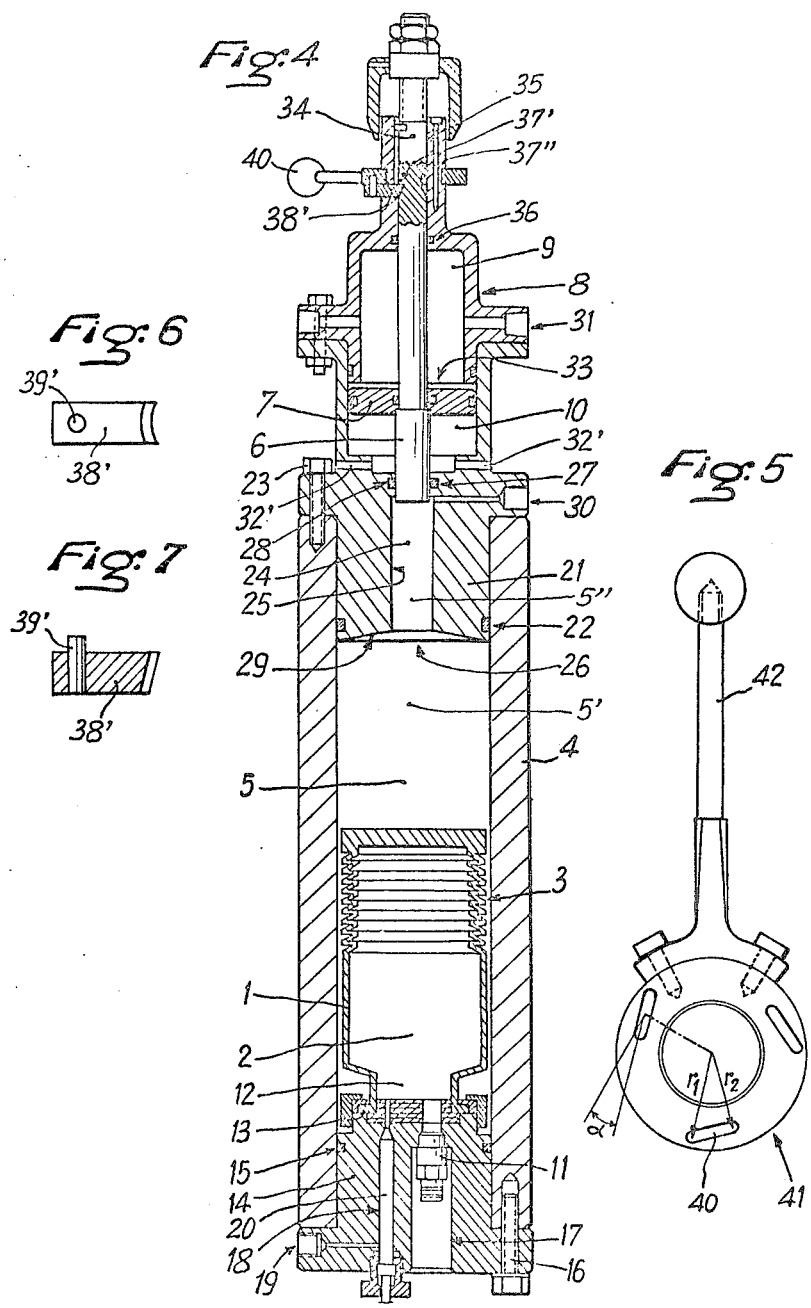

PROCESS AND DEVICE FOR MEASURING THE RATIO OF THE SPECIFIC HEATS OF A FLUID AT A CONSTANT PRESSURE AND A CONSTANT VOLUME

The present invention is related to a method of measuring the ratio of the specific heats of a real gas at a constant pressure $C_P$ and at a constant volume $C_V$ at a given temperature and at a given pressure. The invention is also related to a device for measuring the above-mentioned specific heat ratio.

In accordance with the thermodynamic theory, the ratio of the respective specific heat values, at constant pressure and constant volume, is equal to the ratio of isothermal compressibility and adiabatic compressibility (equation of Reech):

$$\gamma = \frac{k_T}{k_S} = \frac{\left[\frac{\delta V}{\delta P}\right]_T}{\left[\frac{\delta V}{\delta P}\right]_S}$$

wherein $k_T$ (isothermal compressibility) $= -(1/V)\cdot[\delta V/\delta P]_T$ and $k_S$ (adiabatic compressibility) $= -(1/V)\cdot[\delta V/\delta P]_S$.

The value of $\gamma$ was first determined near the atmospheric pressure by the method of F. CLEMENT and C. B. DESORMES (1812).

According to this known method a gas under a pressure $P_1$ higher than atmospheric pressure is introduced into a large container provided with a valve and a pressure gauge. The initial pressure $P_1$ is measured and the valve is opened so that the pressure within the container can drop and reach the value of the atmospheric pressure $P_2$. The valve is shut again immediately. During this virtually adiabatic expansion the temperature will pass from a value $T_1$ to $T_2$ lower than $T_1$, and when the gas within the container again reaches the temperature $T_1$ its pressure equals $P_1'$.

$V_1$ being the volume of one mole of gas under pressure $P_1$, and $V_2$ representing the volume after adiabatic expansion when the pressure reaches the value $P_2$, the following equation (1) is applicable:

$$P_1 \cdot V_1^\gamma = P_2 \cdot V_2^\gamma$$

When the temperature $T_1$ has been reached again, after adiabatic expansion, the gas pressure equals $P_1'$, and since in the experimental apparatus one mole of the gas occupies a volume $V_2$, the container having been sealed after the expansion, the following equation (2) is applicable:

$$P_2 \cdot V_2 = P_1' \cdot V_2$$

When eliminating $V_1$ and $V_2$ between the equations (1) and (2) the following equation is obtained:

$$\gamma = \frac{\log P_1 - \log P_2}{\log P_1 - \log P_1'}$$

(Thermodynamic for Chemists, by Samuel Glasstonne, published by D. Van Nostrand Inc. 1947, Princetown, New Jersey, Edition 1960, page 59). The expansion process applied in this method is adiabatic but not reversible, on account of the fact that the gaseous mass is not constant since part of this gas is ejected from the container during said expansion. Under these conditions the value of $\gamma$ can only be determined approximately.

More recently the $\gamma$ coefficient for real gases was determined by using state equations.

It should be recalled that the specific heat values at zero pressure $C_V°$ can be determined by interpreting the spectroscopic data and the specific heat values at zero pressure $C_P°$ can be inferred from the relation $C_P° - C_V° = R$, wherein R is the constant of the ideal gases, i.e. 8.314 Joules/moles/°K.

The extension of the specific heat values to other pressures is obtained by applying the thermodynamic laws $$C_P - C_P° = - T \int_0^P \left[\frac{\delta^2 V}{\delta T^2}\right]_P \cdot dP$$

$$C_V - C_V° = + T \int_0^V \left[\frac{\delta^2 P}{\delta T^2}\right]_V \cdot dV$$

(same reference "Thermodynamic for Chemists", page 168 (21.12) and page 171 (21.19).

Knowing $C_V°$ and $C_P°$ and the differences $(C_P - C_P°)$ and $(C_V - C_V°)$ it is possible to calculate:

$$\gamma = \frac{(C_P - C_P°) + C_P°}{(C_V - C_V°) + C_V°} = \frac{C_P}{C_V}$$

These differences $(C_P - C_P°)$ and $(C_V - C_V°)$ are calculated from two derivations followed by an integration on a state equation:

$$f(P, V, T) = 0.$$

Now there exists numerous state equations more or less adapted to the solution of the particular problems with which research workers are confronted in the various domains of thermodynamics. In general these formulas are complex; the most widely used is the formula of Benedict M., Webb G. B., Ribin L. C. given in its original version by J. Chem. Phy. 8, 334 (1940).

The operations carried out on these formulas, two successive derivations followed by an integration, are delicate operations in themselves and lead to results which vary according to the equation which is used.

The specific heat ratio can also be inferred from the velocity of the ultrasonic waves in the gases.

Within the limits of low frequencies and low amplitudes, the velocity of the sound u in a gas having a volumic mass p and an adiabatic compressibility $k_S$ is given by the relation $$u = (k_S \cdot \rho)^{-\frac{1}{2}}$$

from the above-cited formula of REECH, one draws $k_S = k_T/\gamma$ thus $$u = [k_T \rho / \gamma]^{-\frac{1}{2}}$$

so that $\gamma = u^2 \cdot k_T \rho$ and since $\rho = 1/V$ one obtains $$\gamma = u^2 \cdot \left[ -\frac{1}{V} \cdot \left[\frac{\gamma V}{\gamma P}\right]_T \right] \cdot \frac{1}{V}$$

$$\gamma = -\frac{u^2}{V^2} \left[\frac{\delta V}{\delta P}\right]_T$$

The velocity of sound u is measured, V is known and $[\delta V/\delta P]_T$ is determined by a single derivation of a state equation.

Thus, this method would seem to be more reliable than the preceding one if one did not have to take into account the fact that the sound velocity varies as a function of the wave frequency.

It is also possible to resort to calorimetric methods wherein the quantity of heat supplied to the gas and the corresponding temperature rise are successively measured:

at constant volume: $dQ = C_V dT$ and at constant pressure: $dQ = C_P dT$

It is difficult to apply this method over a considerable range of temperatures and pressures, since in the various apparatus the caloric capacity of the container is always higher than that of the examined content.

The method according to the invention palliates the drawbacks exhibited by the various methods described above, since it consists in calculating the coefficient by direct application of the REECH formula, expressed in terms of a pressure difference ratio, where the pressures can be measured with a high sensitiveness while the apparatus used allow the measures to be applied within a wide range of temperatures and pressures.

In the method according to the invention, the object of which is the measuring of the ratio of the specific heat of a fluid at a constant pressure $C_P$ and at a constant volume $C_V$, corresponding to a given temperature $T_o$ and a given pressure $P_o$, a determined mass of said fluid is adiabatically compressed, the maximum pressure $P_S$ is detected and its value is measured, the pressure stabilization value $P_T$ is measured, and the pressure difference ratio $P_S - P_o / P_T - P_o$ is calculated.

In this method a constant gas mass follows a thermodynamic curve which successively comprises an adiabatic and reversible, and, therefore isentropic evolution, between an initial state $P_o V_o T_o$ and a final state $P_S V_S T_S$ followed by an evolution at constant volume, or isochoric evolution, between $P_S$, $V_S T_S$ and $P_T V_S T_o$, this latter figurative point being placed on the isotherm of the figurative point of the beginning of the curve.

The REECH formula reads as follows:

$$\gamma = [\delta V/\delta P]_T [\delta V/\delta P]_S$$

In the experimental adiabatic evolution and in accordance with the isothermic curve which connects the final state of the isochoric evolution with the initial state of the adiabatic evolution, the volume variations are equal.

It is admitted that for small pressure variations the coefficient $\gamma$ remains constant, which means that the preceding relation can be formulated as follows:

$$\gamma = (\Delta P)_S / (\Delta P)_T$$

or $$\gamma = (P_S - P_o)/(P_T - T_o)$$

In order to allow the compression to be considered as an adiabatic compression, it must be achieved during a time interval of a few hundreths of a second. With a view to ensuring the reversibility conditions said gas is submitted to a volume reduction which is at the most equal to one hundredth of the initial volume. Finally, in order to ensure that the pressure $P_T$ is measured under sufficient stabilization conditions to make sure that the gas temperature has come back substantially to the initial temperature $T_o$, $P_T$ is measured after a time interval which is sufficient to ensure said stabilization.

A device according to the invention for measuring the ratio of the specific heats of a gas at a constant pressure $C_P$ and at a constant volume $C_V$, corresponding to a given temperature $T_o$ and a given pressure $P_o$, comprises a closed container, made of elastic material and having a thermal conductivity lower than $10^{-2}$ watts/Cm.C° (or watts per centimeters · degrees Celsius), which contains said fluid, said container being placed within a mercury-containing enclosure under pressure into which enters a solid piston having an adjustable stroke length under the action of instantaneously unlockable locking means, and a pressure pick-up means connected with the inside of the elastic container, the entire assembly being immersed in a bath, the temperature of which is kept constant.

In a preferred embodiment of the invention the elastic container is constituted by a cylindrical diaphragm, a portion of which is bellow-shaped.

In this same embodiment the solid piston is integral with a pneumatic piston of larger diameter which moves within an associated cylinder from a preliminary position, wherein it is maintained by the instantaneously unlockable locking means, to a compression position.

In various embodiments, the instantaneously unlockable locking means are constituted by a so-called "wolf's teeth" mechanism.

With a view to providing repeatable measurements for a given experimental pressure, the mercury-containing enclosure under pressure has a temperature drift lower than $5.10^{-2}$° C. per hour. In order to obtain sufficient precision for each pressure measurement, the pressure pick-up device is of the piezo-resistive type and is able to detect pressure variations as small as one ten-thousandth of the value of the measuring pressure, with a responding time shorter than one thousand of a second.

In the various embodiments the end of the solid piston which enters the cell moves in a translational manner in a cylinder which opens into the cell, said cylinder constituting the internal portion of a passage provided along the axis of a plug of the cell, the remaining portion of said passage being constituted by a portion having reduced cross-sectional dimensions which serves to guide the piston while said cell plug delimits the inner volume of the mercury-containing cell by a portion of the surface of said cylinder and by an annular surface which surrounds the aperture through which said cylinder opens into the cell.

In a preferred embodiment of the invention the annular surface which surrounds the aperture through which the cylinder opens into the cell has the shape of a truncated one, the apex of which is directed outwardly with respect to the cell and wherein a gas drain valve is provided at the bottom of the cylinder immediately before the reduced diameter portion of the above-mentioned passage.

The invention will be described hereinbelow in a more detailed manner with reference to the appended Figures which are given by way of illustration but not of limitation:

FIG. 4 is a detailed cross-sectional view of the device.

FIG. 5 shows the driving crank and catch driving ring.

FIG. 6 shows a locking catch (planar view).

FIG. 7 also shows a locking catch (sectional view).

Figure 1:
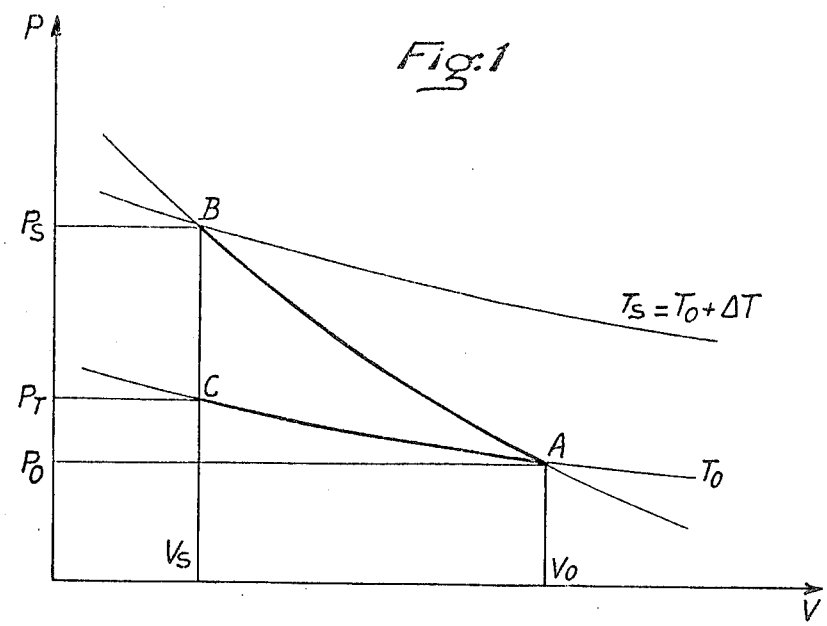
FIG. 1 is a thermodynamic diagram (pressure-volume diagram).

Referring to FIG. 1, the pressure-volume diagram shows the figurative thermodynamic curve representing the states of a fluid under examination. Starting from the initial state $P_oV_oT_o$ represented by point A, the gas follows an adiabatic and reversible evolution, which means an isentropic evolution, from A to B which is figurative of the state $P_S V_S T_S$ such as:

$$V_S = V_o - \Delta V \text{ and } T_S = T_o + \Delta T$$

The gas is then submitted to an evolution at constant volume from B to C having the characteristic $P_T V_S T_o$.

Point C is located on isotherm $T_o$ passing through point A.

Figure 2:
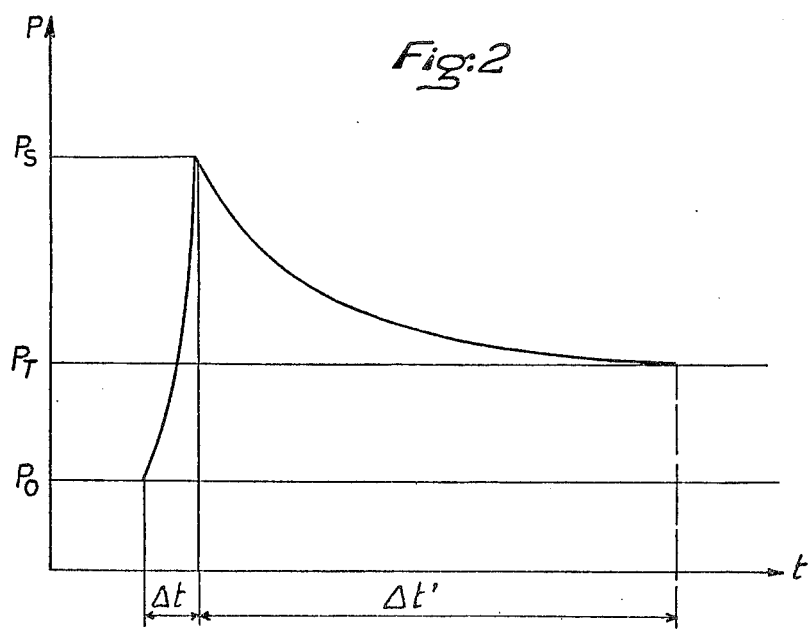
FIG. 2 shows the profile of the pressure in function of time.

FIG. 2 shows the evolution of the pressure as a function of time during the evolutions described with respect to FIG. 1. The time interval of the compression phase is clearly visible: $\Delta t$ has a value of several hundredths of a second. The time interval $\Delta t'$ is also indicated, which must elapse before measuring the value of $P_t$ so as to ensure that the latter is substantially located on the isotherm $T_o$. The time interval $\Delta t'$ must amount to at least 100 seconds, said value of $\Delta t'$ corresponding to the dispersal of at least 99% of the energy transmitted to the gas during the compression phase.

Figure 3:
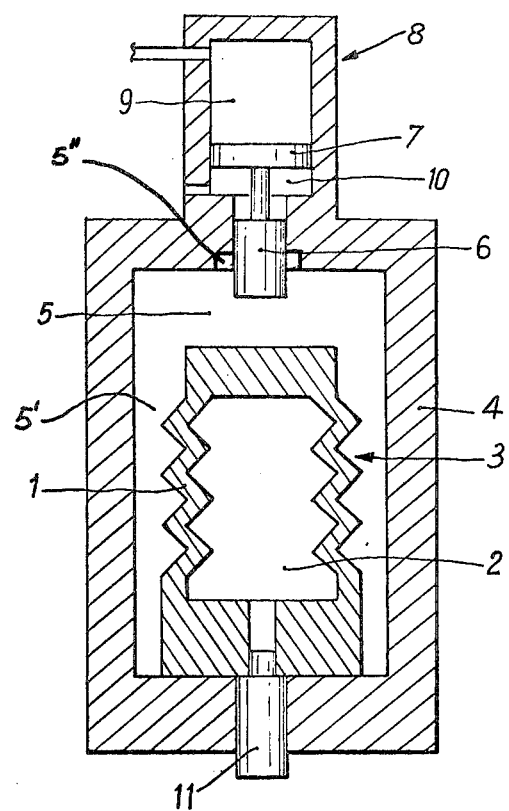
FIG. 3 shows a simplified scheme of the device according to the invention.

FIG. 3 is a simplified schematical view illustrating the principle of the device for carrying out the method according to the invention.

FIG. 3 shows a container 1 having an inner cavity 2 which contains a fluid to be examined.

Container 1 is made of an elastic material, the thermal conductivity of which is lower than $10^{-2}$ watts/cm/degrees Celsius, such as TEFLON®, a product known per se.

The container 1, which as shown in the Figure has a cylindrical shape, is partially constituted by bellows 3 which serve to enhance its expanding capacity without excessively increasing its outer global surface. Container 1 is placed in a steel cell 4, the inner space 5 of which comprises two coaxial cylindrical space portions, a space portion 5' having an inner diameter slightly larger than the outer diameter of container 1 and a portion 5" having a diameter slightly larger than the diameter of piston 6 which is longitudinally movable in the direction of the axis which is common to spaces 5' and 5". The thus delimited space 5 is filled with mercury. Piston 6 is integral with a coaxial piston 7 which has a diameter larger than that of piston 6. Piston 7 moves in a cylinder 8 dividing said cylinder into two compartments one of which, compartment 9 opposite to piston 6, contains a gas volume and is connected to outer pressurizing means (not shown), while the other compartment, compartment 10 located on the side of piston 6, communicates with the atmosphere. A pressure pick-up device 11 of the piezo-resistive type is connected to the inner space 2 of container 1. The entire assembly is immersed in a bath, the temperature T of which is controlled.

FIG. 4 is a longitudinal section of a device for measuring the coefficient $\gamma$ (the ratio of the specific heats at a constant pressure $C_p$ and at a constant volume $C_V$) of a real gas; the same arrangements and the same elements which were described with reference to the simplified schematic view of FIG. 3 are to be found again in FIG. 4.

The cylindrical container 1 has an outer diameter slightly smaller than the inner diameter of cell 4 which has also a cylindrical shape.

Container 1 is provided with an aperture 12 surrounded by a collar 13 adapted to be fixed, by any convenient means known per se, to the inner wall of plug 14 sealing one end of the cylindrical cell 4.

Plug 14 is provided with a sealing ring 15 placed in a groove provided on the periphery of said plug, and with fixing pins such as 16. Plug 14 comprises two recesses one of which, i.e. recess 17, is adapted to contain a pressure pick-up 11 opening into the inner cavity 2, while the second recess, shown at 18, defines an inlet an outlet passage for the gas to be examined. Recess 18 is connected to this end to a nozzle 19 which is connected, in turn, to a conduit (not shown) and comprises a closing device including a valve needle 20.

Cylindrical cell 4 is delimited at its end opposite to plug 14 and container 1 by a cell plug and piston support 21. Plug 21 is provided with a sealing ring 22 and with fixing pins such as 23.

Plug 21 has an axial passage 24 extending through said plug and comprising a cylindrical portion 25 delimiting an inner space 5" which is part of the inner space 5 of cell 4; furthermore, said cylindrical portion 25 opens into space 5' through a circular orifice 26; axial passage 24 further comprises a cylindrical portion 27 which is an extension of cylindrical portion 25 and has a diameter that is several hundredths of a millimeter larger than the diameter of piston 6. This cylindrical portion 27 constitutes a portion in which the piston 6 slides.

A groove containing a sealing ring 28 is provided in the inner wall of the reduced-diameter portion of the cylindrical passage.

Plug 21 is in contact with the mercury contained in the cell 4 along the inner surface of cylinder 25 and along an annular surface 29 surrounding aperture 26 through which cylinder 25 opens into the cell.

Annular surface 29 has a frusto-conical shape, the apex of which is located on the axis of cylinder 25 and directed away from container 1.

The orifice of conduit 30 connected to a gas-draining device is located on the bottom of cylinder 25 immediately before the reduced-diameter portion 27.

Piston 6 is integral with a piston 7, the diameter of which is larger than that of piston 6. Piston 7 moves within a cylinder 8 and divides said cylinder into two compartments one of which, i.e. compartment 9 opposite to piston 6, contains a gas volume and is connected through a nozzle 31 to an external pressurizing means (not shown), while the other compartment, i.e. compartment 10 adjacent to piston 6, communicates with the atmosphere through nozzles 32' and 32". In chamber 9 a portion having a reduced diameter and extending in the direction opposite to cell 4 constitutes a stop 33 adapted to limit the stroke length of piston 7 to such a value that piston 6 has its end located at a distance of several millimeters from the beginning of the reduced diameter portion 27, when the upper stroke end is reached (with reference to the representation of FIG. 4).

Piston 6 integral with piston 7 is also integral with a coaxial rod 34 moving in a cylinder 35 beyond cylinder 8 with a play of several hundredths of a millimeter. Cylinder 35 is isolated from cylinder 8 by a sealing ring 36.

An unlockable locking device known per se under the name of "wolf's teeth mechanism" is mounted on rod 34.

In such an instantaneously unlockable locking device, stops 37', 37'', 37''', only two of which, i.e. stops 37' and 37''', are visible in FIG. 4, cooperate with an equal number of catches such as the one shown at 38' in FIG. 6 (planar view) and in FIG. 7 (sectional view). Each catch is provided with a cylindrical stud 39' mounted by force in a cylindrical recess having the same dimensions, in such a manner that each stud protrudes from the upper surface of the associated catch, the protruding portion of the stud slidingly engaging an equal number of rectilinear grooves such as 40' provided in the lower face of a driving ring 41 adapted to drive the catches and on which a driving crank, or crank pin, 42 is fixed.

FIG. 5 shows the driving ring 41 with the crank 42. It will be seen that an angle is defined between the grooves such as 40' and the circle which is concentric to the ring and passes through the center of each groove. This angle is equal to about ten sexagesimal degrees. Due to this angle the end portions of the center of each stud are separated by distances $r_1$ and $r_2$ which are so selected that $r_1-r_2$ is larger than the depth of the stop 37' on rod 34.

With a view to measuring the coefficient $\gamma$ of a real gas at a selected pressure:

the assembly of movable pistons 6, 7, 34 is checked so as to make sure that it is in its rest position on stop 33;

container 1 is filled with the real gas under conditions corresponding to its initial $P_oT_o$ state;

the pressure of the air in compartment 9 is increased to the necessary value to cause piston 6, while penetrating the cylinder 25 communicating with cell 4, to exert pressure $P_S$ within a very short space of time. The stroke length of piston 6 is then adjusted;

by means of crank 42 and the woolf's teeth mechanism, rod 34 is unlocked, whereby the pressure of the gas contained in container 1 is brought to the valve $P_S$ within a time period of $\Delta t$.

The compression time $\Delta t$ may be controlled by feelers measuring the displacement of the piston, and may be measured by a quartz clock. $\Delta t$ is measured directly on the continuous recording of the pressure profile as indicated in FIG. 2.

When a period of time of 100 seconds has elapsed $P_T$ is measured.

One single pressure pick-up allows the ratio $\gamma = \Delta P_S/\Delta P_T$ to be measured; thus it is not necessary to calibrate the pressure pick-up. The resolution of the piezo-resistive pick-up must be higher than $10^{-4}$. The pick-up, which is analogous to a bridge consisting of resistive gauges, is fed with a current provided by a high-stability current source. A stabilized voltage source must be used in order to counter-balance the signal produced by the pick-up and act upon the dynamic of the amplifier.

In order to obtain the signal, it is possible to only detect the crest $\Delta P_S$ of the adiabatic pressure peek and the asymptotic $\Delta P_T$; it is also possible to record. The first mentioned method requires the use of a device similar to those used in the field of detection of high-speed chromatographic peeks (crest detector) and produces a blind measure of the pressure variations. The second one of the above mentioned methods requires the use of U.V. or magnetic high-speed recorders, but allows the examined phenomena to be visualized. This latter method also allows the values of $\Delta P_S$ and $\Delta P_T$ (and thus $\gamma$), and the value of the compression time $\Delta t$ to be directly measured on the recording.

The method according to the invention is an entirely experimental one and at no time involves the use of a state equation or a theoretical computation which it would not be possible to check directly. This method can thus be used as an auxiliary means for determining the values $\gamma$ and n which are involved in the computation of the transactions on volumes of natural or other gases.

The fact that the values obtained lie within the average range of the results obtained by the various methods used for examining pure gases is by no means construed as being a justification; this fact only shows a posteriori the coherent nature of the state equations used.

This experimental determination of $\gamma$ leads to the compution of n on the basis of experimentally determined $\gamma$ and Z values, and the substitution of the experimental n value for the former value which, for all the natural gases containing essentially methane is:

$n = \gamma = 1.31$ (supposedly perfect gas)

For the given $P_o$ and $T_o$ values and a measured $\gamma$ value of 1.49, n is found to equal 1.347; thus for a given natural gas deposit, an increase of the output of $\Delta Q = 4.8 \times 10^5 m^3$ for $Q = 10^{10} m^3$ gas $\Delta Q/Q = 4.8 \times 10^{-5}$ is obtained, which is appreciable in the case of transactions extending over long periods of time.

The invention is not limited to the examples described hereinabove; many modifications and variants may be envisaged by those skilled in the art without departing from the scope of the invention as defined in the appended claims.

What is claimed is:

1. A method for measuring the ratio $\gamma$ of the specific heats of a fluid at a given constant pressure $C_P$ and at a constant volume $C_V$ corresponding to a given temperature $T_o$ and a given pressure $P_o$, comprising the steps of adiabatically compressing a predetermined mass of said fluid, detecting the maximum value of pressure $P_S$, measuring said maximum $P_S$ value, measuring the stabilization pressure $P_T$ and computing said specific heat ratio according to the equation:

$\gamma = (P_S - P_o)/(P_T - P_o)$

2. The method of claim 1, wherein said fluid is adiabatically compressed for less than 0.1 second by reducing the volume of said fluid by not more than one hundredth of its initial volume, the volume $P_T$ being then measured after a convenient period of time.

3. A device for measuring the $\gamma$ ratio of the specific heats of a fluid at a given constant pressure $C_P$ and at a constant volume $C_V$ corresponding to a given temperature $T_o$ and at a given pressure $P_o$, said device comprising a container made of elastic material having a thermal conductivity of less than $10^{-2}$ watts/cm.° C., said container being adapted to contain said fluid and being placed in a pressurized cell containing mercury, a solid piston having an adjustable stroke length, one end of which is adapted to penetrate said pressurized cell under the action of instantaneously unlockable locking means, and a pressure pick-up connected to the inner space of said elastic container, all of the above recited elements being immersed in a constant-temperature bath.

4. The device of claim 3, wherein said elastic container is constituted by a cylindrical diaphragm, a portion of which is bellow-shaped.

5. The device of claim 4, wherein said annular surface surrounding said orifice through which said cylinder opens into said cell has a frusto-conical shape, the apex of which is oriented away from said cell, and wherein a gas-draining device is located on the bottom of said cylinder before said-reduced diameter portion, in the immediated proximity thereof.

6. The device of claim 3, wherein said solid piston is integral with a pneumatic piston having dimensions larger than those of the solid piston and displaceable within an associated cylinder from a preliminary position wherein it is maintained by said instantaneously unlockable locking means to a compression position.

7. The device of claim 6, wherein said instantaneously unlockable locking means are constituted by a wolf's teeth mechanism.

8. The device of claim 3, wherein the temperature of said pressurized cell containing mercury drifts by less than $5.10^{-2}$ ° C. per hour.

9. The device of claim 3, wherein said pressure pick-up is a piezo-resistive pick-up capable of detecting pressure variations of as small an amount as one ten thousandth of the value of the pressure being measured.

10. The device of claim 3, wherein the end of said solid piston, which is adapted to penetrate said cell, moves in a translational manner within a cylinder opening into said cell, said cylinder defining an inner portion of a passage extending in the direction of the axis of a plug sealing said cell, the remaining portion of said passage having reduced cross-sectional dimensions and serving to guide the piston, said plug being adapted to delimit the inner volume of the cell containing mercury by a portion of the surface of said cylinder and by an annular surface surrounding the orifice through which the said cylinder opens into said cell.

* * * * *